(12) United States Patent
Lu et al.

(10) Patent No.: US 9,573,901 B2
(45) Date of Patent: Feb. 21, 2017

(54) CRYSTAL FORM OF CHIDAMIDE, PREPARATION METHOD AND USE THEREOF

(71) Applicant: SHENZHEN CHIPSCREEN BIOSCIENCES, LTD., Shenzhen, Guangdong (CN)

(72) Inventors: Xianping Lu, Shenzhen (CN); Zhibin Li, Shenzhen (CN)

(73) Assignee: SHENZHEN CHIPSCREEN BIOSCIENCES, LTD., Shenzhen, Guangdong (CN)

( * ) Notice: Subject to any disclaimer, the term of this patent is extended or adjusted under 35 U.S.C. 154(b) by 0 days.

(21) Appl. No.: 14/646,371

(22) PCT Filed: Dec. 18, 2012

(86) PCT No.: PCT/CN2012/086841
§ 371 (c)(1),
(2) Date: May 20, 2015

(87) PCT Pub. No.: WO2014/082354
PCT Pub. Date: Jun. 5, 2014

(65) Prior Publication Data
US 2015/0299126 A1    Oct. 22, 2015

(30) Foreign Application Priority Data
Nov. 27, 2012  (CN) .......................... 2012 1 0489178

(51) Int. Cl.
*C07D 213/82*    (2006.01)
*C07D 213/04*    (2006.01)
(Continued)

(52) U.S. Cl.
CPC .......... *C07D 213/82* (2013.01); *A61K 31/4406* (2013.01); *C07D 213/04* (2013.01);
(Continued)

(58) Field of Classification Search
CPC ... C07D 213/82; C07D 213/04; C07D 213/24; C07D 213/54; C07D 213/56; A61K 31/4406; C07B 2200/13
(Continued)

(56) References Cited

U.S. PATENT DOCUMENTS 7,244,751 B2    7/2007 Lu et al.

FOREIGN PATENT DOCUMENTS

CN    1513839 A    7/2004
WO    2004/071400 A2    8/2004

OTHER PUBLICATIONS

Gong; Biochem. J. 2012 443, 735-746.*
(Continued)

*Primary Examiner* — Noble Jarrell
*Assistant Examiner* — Daniel Carcanague
(74) *Attorney, Agent, or Firm* — Maschoff Brennan

(57) ABSTRACT

The present invention belongs to the field of pharmaceutical chemistry, and disclosed are two crystal forms of Childamide, that is, Chidamide crystal form A and Chidamide crystal form B, and the method for preparing the new crystal forms of Chidamide. The Chidamide crystal form A and Chidamide crystal form B of the present invention can be used for preparing drugs for treating diseases related to cell differentiation and proliferation.

3 Claims, 5 Drawing Sheets

(51) Int. Cl.
 C07D 213/24 (2006.01)
 C07D 213/54 (2006.01)
 C07D 213/56 (2006.01)
 A61K 31/4406 (2006.01)
(52) U.S. Cl.
 CPC ......... *C07D 213/24* (2013.01); *C07D 213/54* (2013.01); *C07D 213/56* (2013.01); *C07B 2200/13* (2013.01)
(58) Field of Classification Search
 USPC ........................................................ 546/339
 See application file for complete search history.

(56) References Cited

OTHER PUBLICATIONS

Dong; Cancer Chemother Pharmacol 2012, 69, 1413-1422.*
Hui et al., "Synthesis of chidamide,a new histone deacetylase (HDAC) inhibitor", Chinese Journal of New Drugs, vol. 13, Issue 6, 2004, pp. 536-538.
European Search Report issued May 10, 2016 for European Application No. 12889061.3 filed Dec. 18, 2012.
Caira, "Crystalline Polymorphism of Organic Compounds", Topics in Current Chemistry, Springer, Berlin, Germany, vol. 198, Jan. 1, 1998, pp. 163-208.

* cited by examiner

CRYSTAL FORM OF CHIDAMIDE, PREPARATION METHOD AND USE THEREOF

The present application claims the priority of Chinese patent application No. 201210489178.8 filed on Nov. 27, 2012 with the Chinese Patent Office, titled "Crystal form of chidamide, preparation method and use thereof", which is hereby incorporated by reference in its entirety.

TECHNICAL FIELD OF THE INVENTION

The present invention relates to the field of pharmaceutical chemistry, and particularly to novel chidamide crystal forms A and B, and the preparation method and the use thereof.

BACKGROUND OF THE INVENTION

Chidamide is a novel anticancer drug that is designed and synthesized by Chipscreen Co. Ltd. (Shenzhen, China) with a completely new chemical structure and worldwide intellectual property rights. The chemical name of chidamide is N-(2-amino-4-fluorophenyl)-4-(N-(3-pyridylacryloyl)aminomethyl)benzamide, with chemical structure of formula I:

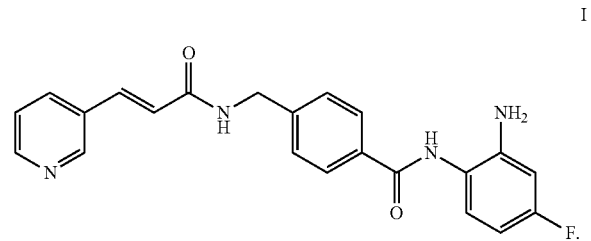 [SMILES: Nc1cc(F)ccc1NC(=O)c1ccc(CNC(=O)/C=C/c2cccnc2)cc1]

I

As described in patent ZL 03139760.3 and U.S. Pat. No. 7,244,751, chidamide has the inhibition activity on histone deacetylases, and can be used in the treatment of differentiation and proliferation-related diseases, such as cancers and psoriasis, and particularly, it possesses excellent therapeutic efficacy on leucocythemia and solid tumors.

Although the preparation method of chidamide was disclosed in patent ZL 03139760.3 and U.S. Pat. No. 7,244,751, it was not indicated whether the product was a crystalline substance, nor whether there was polymorphism for the compound. In the patents mentioned above, the evaluation on the activities of the compound was not performed in solid state, and accordingly, there was no crystal characteristics-related description disclosed.

Crystal form is one of the key factors that affect the quality, therapeutic efficacy and formulation processing performance of the drug substance. Polymorphism refers to the phenomenon that one compound may form two or more molecular spatial arrangements by controlling the conditions and thus form different solid crystals. Polymorphism is a common phenomenon in the development of a drug substance, and is a key factor to affect the quality of a drug product. For different crystal forms of a compound, although they have the same chemical composition, they have different crystal structures, and result in differences in their external morphology, physicochemical properties and biological activities. Different crystal forms of a drug substance tend to be different in solubility, storage stability, hygroscopicity, density and bioavailability. The crystal form of a drug substance directly influences the quality of its pharmaceutical formulation and the absorbing behavior in the human body, and thus influences the therapeutic effect/side effect ratio in human body. Accordingly, it is of great significance to investigate the polymorphism of a drug substance and the preparation methods for different crystal forms.

SUMMARY OF THE INVENTION

Based on the content above, the objective of the present invention is to study, discover and provide novel crystal forms of chidamide, the preparation method and the use thereof.

The purity of chidamide prepared as described in Example 2 of patent ZL 03139760.3 is low (about 95%). As shown by the results of LC/MS in FIG. 1, the product contains 4.7% of N-(2-amino-5-fluorophenyl)-4-(N-(3-pyridylacryloyl)aminomethyl)benzamide of formula II. As shown by the results of $^1$H NMR in FIG. 2, the product contains 1.80% of tetrahydrofuran, which is much higher than the solvent residue limit (0.072%) for the drug substance to be registered specified by International Conference of Harmonizition (ICH). Accordingly, the solid is not suitable for the manufacturing of drug products.

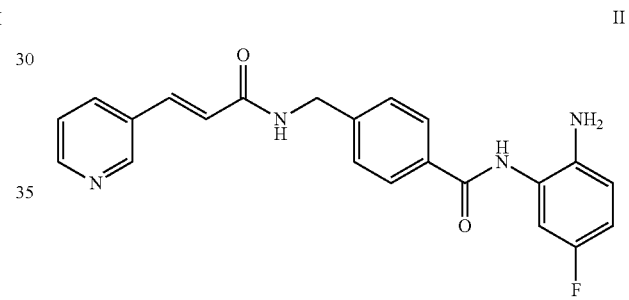

II

By crystallographic methods, two crystal forms of chidamide, i.e., chidamide crystal form A and crystal form B, were investigated, discovered and provided by the present invention.

Novel crystal forms of chidamide have been investigated and characterized by a well-recognized method X-ray powder diffraction method (XRPD) in the present invention. Instrument: X-ray powder diffractometer (D/MAX-1200). Conditions for detection: Cu/K-alpha1 (target), 40KV-40 mA (operating voltage and current), I(max)=2244, 2θ=5-60° (scan range), 0.005/0.06 sec. (scan speed), and λ=1.54056.

The crystal form A of substantially pure chidamide provided herein has an X-ray powder diffraction pattern as shown in FIG. 3. It has the following characteristics: the X-ray powder diffraction pattern has peaks at 2θ of about 4.18°, 6.61°, 8.42°, 12.69°, 17.85°, 18.34°, 19.27°, 20.10°, 20.59°, 21.58°, 23.70°, 23.96°, 25.52°, 27.00°, 27.90°, 29.59°, and 29.94°.

The present invention further studies and characterizes a novel crystal form of chidamide by infrared spectrometry (IR). Instrument: FT-IR NICOLET 6700 (US). Measurement: KBr disc, spectrum range: 400 cm$^{-1}$-4000 cm$^{-1}$, resolution: 4 cm$^{-1}$.

The crystal form A of substantially pure chidamide provided herein has an infrared spectrum as shown in FIG. 4. It has the following characteristics: the infrared spectrum has characteristic absorption peaks at about 3412, 3282, 3199, 3043, 1654, 1615, 1524, 1514, 1497, 1442, 1418, 1332, 1296, 1234, 1198, 1183, 1166 and 1027 cm$^{-1}$.

Other analysis technologies known in the art can also be used to characterize the crystalline form, such as the differential scanning calorimetry (DSC). Instrument: DSC 204 (Germany), temperature ramp rate: 10° C./min, flow rate of nitrogen: 20 mL/min.

The crystal form A of substantially pure chidamide provided herein has a differential scanning calorimetry pattern as shown in FIG. 5, which has the following characteristics that the pattern has an endothermic peak at about 239.4° C.

The crystal form B of substantially pure chidamide provided herein has an X-ray powder diffraction pattern as shown in FIG. 6. It has the following characteristics: the X-ray powder diffraction pattern has peaks at 2θ of about 4.18°, 8.43°, 12.65°, 16.90°, 17.83°, 19.47°, 20.13°, 20.58°, 21.22°, 21.54°, 21.92°, 23.94°, 25.55°, 26.98°, 27.92°, 29.58°, and 29.90°.

The crystal form B of substantially pure chidamide provided herein has an infrared spectrum as shown in FIG. 7. It has the following characteristics: the infrared spectrum has characteristic absorption peaks at about 3412, 3327, 3272, 3196, 3043, 1653, 1619, 1570, 1515, 1496, 1444, 1419, 1331, 1357, 1296, 1278, 1267, 1232, 1198, 1184, 1166 and 1038 cm$^{-1}$.

The crystal form B of substantially pure chidamide provided herein has a differential scanning calorimetry pattern as shown in FIG. 8, which has the following characteristics that the pattern has endothermic peaks at about 214.1° C. and 241.2° C.

It should be noted that, in terms of the X-ray powder diffraction peaks of the crystalline forms above, 2θ of the X-ray powder diffraction pattern may give rise to a slightly change between one machine and another, as well as between one sample and another. The numerical values thereof may differ by about one unit, or about 0.8 unit, or about 0.5 unit, or about 0.3 unit, or about 0.1 unit. Thus, the given numerical values should not be considered as absolute.

The experimental results show that both the chidamide crystal form A and the chidamide crystal form B described herein have favorable performance in terms of solubility, and thereby have high bioavailability.

The present invention further provides a method for preparing the chidamide crystal form A and crystal form B with high purity (>99%) and free of solvent residue.

The method for preparing the chidamide crystal form A provided herein comprises:

Step 1: chidamide is added to 2 mol/L dilute hydrochloric acid solution, dissolved by stirring at room temperature and diluted with water; to the resultant solution is added dropwise 2 mol/L NaOH solution, stirred for 30 min, and then filtered; wherein the weight ratio between chidamide and the dilute hydrochloric acid solution in Step 1 is in the range from 1:4.2 to 1:4.4, the weight ratio between chidamide and water is in the range from 1:25 to 1:30, and the weight ratio between chidamide and NaOH solution is in the range from 1:2.5 to 1:2.7;

Step 2: the resultant solid is collected, and added to water; to the mixture is added dropwise 2 mol/L NaOH solution, stirred for 60 min, and then filtered; the resultant solid is collected, washed with water to a pH value from 5 to 7, and then dried; wherein the weight ratio between chidamide and water in Step 2 is in the range from 1:15 to 1:25, and the weight ratio between chidamide and NaOH solution is in the range from 1:1.5 to 1:2.0.

Preferably, the drying process in Step 2 was drying under vacuum at 80° C. for 24 h.

The preparation method for the chidamide crystal form B provided herein was as follows: the chidamide crystal form A is added to dimethyl sulfoxide and dissolved by stirred at room temperature; to the resultant solution is added dropwise water, stirred for 30 min, and then filtered; the resultant solid is collected and dried to give the compound; wherein the weight ratio between the chidamide crystal form A and dimethyl sulfoxide is in the range from 1:10 to 1:20, and the weight ratio between the chidamide crystal form A and water is in the range from 1:100 to 1:200.

Preferably, the drying process was drying under vacuum at 80° C. for 24 h.

The purities of the crystal form A and the crystal form B obtained by the preparation methods for the chidamide crystal form A and crystal form B described herein were both >99.0%.

The stability of the chidamide crystal form A and the chidamide crystal form B described herein was tested at high temperature (60° C.), high humidity (90%±5%) and strong light exposure (4500 Lx±500 Lx). The results indicated that both the chidamide crystal form A and the chidamide crystal form B keep the original crystal form, and no significant change was observed for the content and the total impurity amount. Both the chidamide crystal form A and the chidamide crystal form B are suitable for the manufacturing of drug products and long-term storage. The chidamide crystal form A and the chidamide crystal form B described herein have excellent performance in terms of oral absorption and inhibition of cell differentiation and proliferation. Additionally, both crystal forms have low toxicity and favorable storage and treatment stability, and can be used in the preparation of a medicament for treating cell differentiation and proliferation-related diseases. Thus, the present invention provides the use of the chidamide crystal form A and the chidamide crystal form B in the preparation of a medicament for treating cell differentiation and proliferation-related diseases.

Further, the cell differentiation and proliferation-related diseases are selected from cancers or psoriasis, wherein the cancers include leucocythemia or solid tumors.

The novel crystal forms of chidamide described herein can be further prepared into various solid dosage forms for oral administration, such as tablet, capsule or granule.

The pharmaceutical formulation for the treatment of cell differentiation and proliferation-related diseases described herein comprises the chidamide crystal form A or/and the chidamide crystal form B, and pharmaceutically acceptable excipients. In some embodiments, the pharmaceutical formulation comprises the chidamide crystal form A and pharmaceutically acceptable excipients; and in some embodiments, the pharmaceutical formulation comprises the chidamide crystal form B and pharmaceutically acceptable excipients; and in some embodiments, the pharmaceutical formulation comprises a mixture of the chidamide crystal form A and the chidamide crystal form B, and pharmaceutically acceptable excipients.

In some specific embodiments, the formulation contains 5-20% of the chidamide crystal form A or/and the chidamide crystal form B, and 80-95% of the pharmaceutically-acceptable excipients. In such dosage forms, the active compound was mixed with at least one of the pharmaceutically acceptable inert excipients or carriers, such as sodium citrate, calcium phosphate, filler, adhesive, humectant, disintegrant, retardant, absorption enhancer, wetting agent, absorbent or lubricant and a mixture thereof. The examples of filler include starch, lactose, sucrose, glucose, mannitol and silicic acid; the examples of adhesive include carboxymethyl cellulose, alginate, gelatin, polyvinyl pyrrolidone, sucrose and acacia; the example of humectant include glycerol; the examples of disintegrant include agar, calcium carbonate, potato starch or cassava starch, alginic acid, some silicates and sodium carbonates, low substituted hydroxypropyl cellulose; the example of retardant solution includes paraffin; the example of absorption enhancer includes quaternary amine compounds; the examples of wetting agent include hexadecanol and glycerin monostearate; the examples of absorbent include kaolin and bentonite; the examples of lubricant include talc powder, calcium stearate, magnesium stearate, solid polyethylene glycol and sodium lauryl sulfate.

EXAMPLES

The crystal forms of chidamide, and the preparation methods and the use thereof are disclosed in the Examples of the present invention. The present invention can be implemented by properly modifying the processing parameters by those skilled in the art with reference to the content herein. Particularly, it should be noted that all similar replacements and modifications are apparent to those skilled in the art, all of which are regarded to be included in the present invention. The method of the present invention has been described by preferred examples, and it is apparent that modification, or proper change and the combination thereof can be made to the method described herein by those skilled in the art, without departing from the content, spirit and scope of the invention, in order to achieve and apply the techniques disclosed in the present invention.

For better understanding the present invention, it will be further described with reference to specific examples below. The percentage described herein refers to the weight percentage, unless otherwise indicated. All numerical ranges, such as measurement units, reaction conditions, and the physical states or percentages of compounds, described in the specification are provided for clear reference. Expected results can also be achieved by those skilled in the art when the present invention is practiced with temperatures, concentrations or quantities, etc. outside the range or different from individual values.

Experiment Methods

Test conditions for X-ray powder diffraction: Instrument: D/MAX-1200 (Japan); radiation source: Cu-Kα (40 kV, 40mA).

Test conditions for infrared spectrum: Instrument: FT-IR NICOLET 6700 (US); KBr disc.

Test conditions for differential scanning calorimetry: Instrument: DSC 204 (Germany); temperature ramp rate: 10° C./min; flow rate of nitrogen: 20 mL/min.

Test conditions for proton magnetic resonance: Instrument: AV-400 (Germany); Solvent: DMSO-d6.

Example 1

Figure 1:
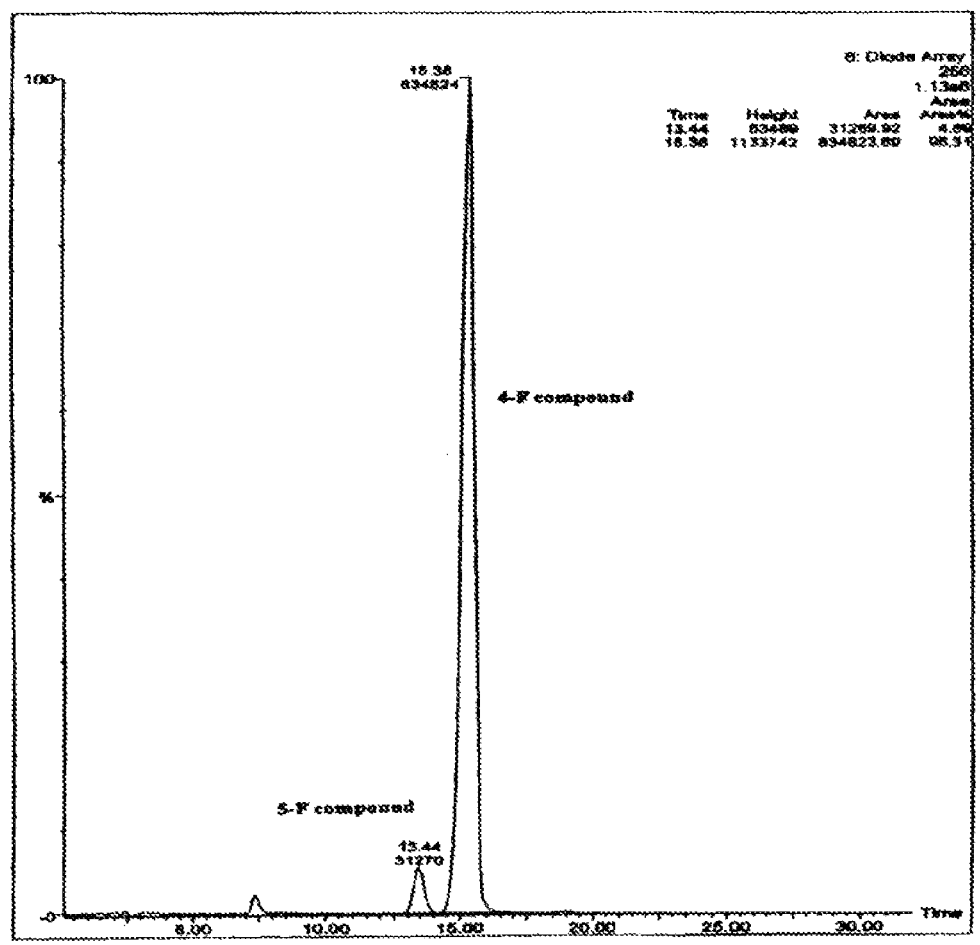
FIG. 1 is the HPLC chromatogram of the solid prepared according to Example 2 of patent ZL 03139760.3.
Figure 2:
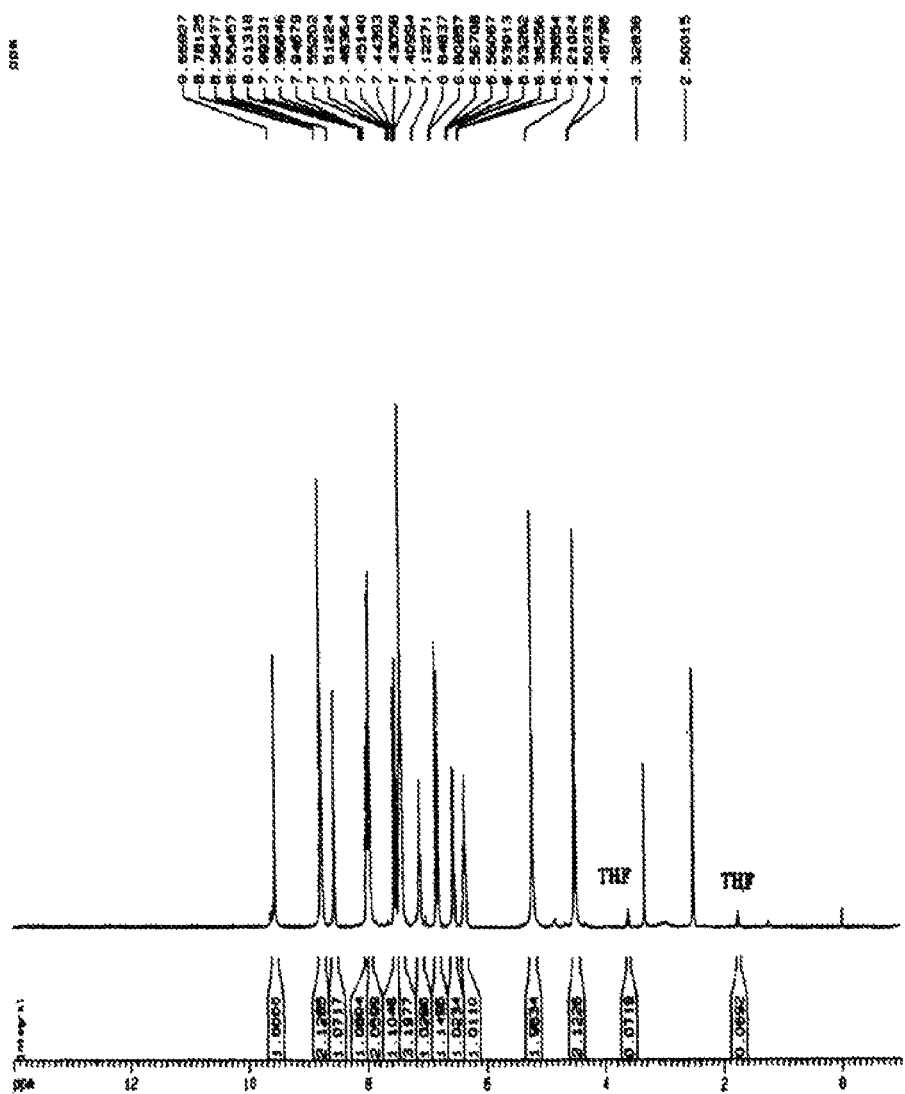
FIG. 2 is the $^1$H NMR spectrum of the solid prepared according to Example 2 of patent ZL 03139760.3.
Figure 3:
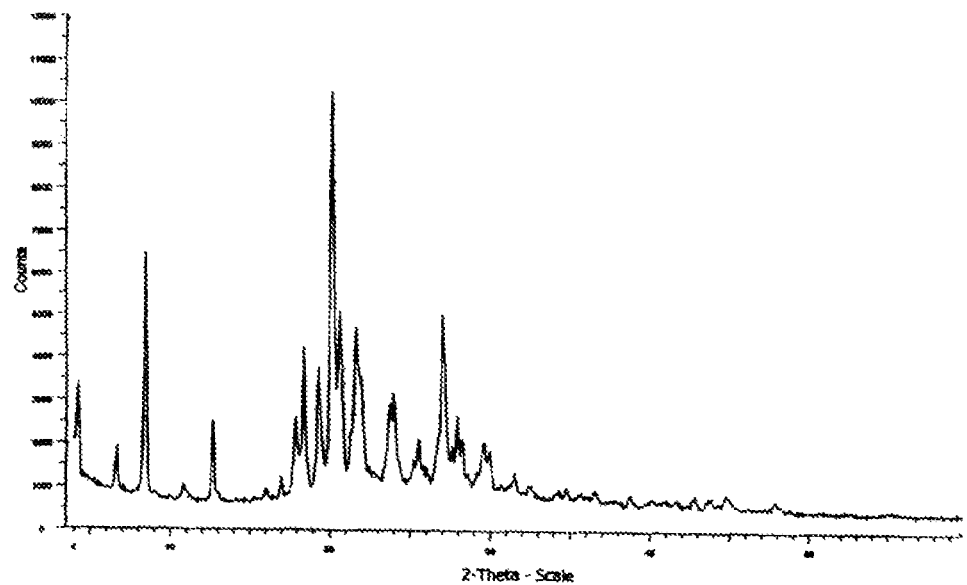
FIG. 3 is the X-ray powder diffraction pattern of the chidamide crystal form A provided in Example 1 of the present invention, which is obtained by irradiation with cooper Kα ray. In the X-ray powder diffraction pattern, the ordinate represents diffraction intensity expressed in counts per second (cps), and the abscissa represents diffraction angle 2θ expressed in degree.
Figure 4:
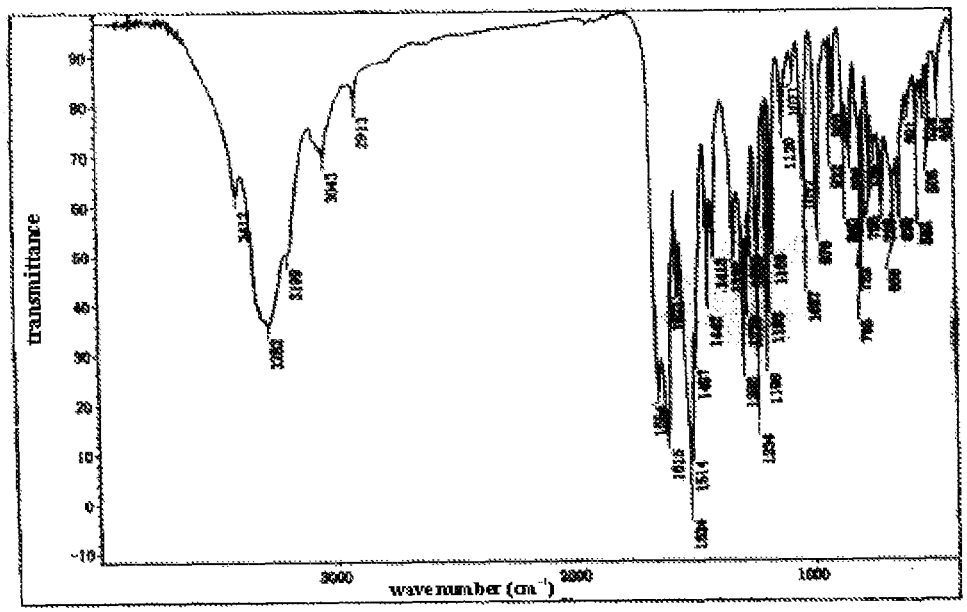
FIG. 4 is an infrared spectrum pattern of the chidamide crystal form A provided by Example 1 of the present invention. The ordinate represents light transmittance (T) expressed in percentage (%); and the abscissa represents wave number expressed in $cm^{-1}$.
Figure 5:
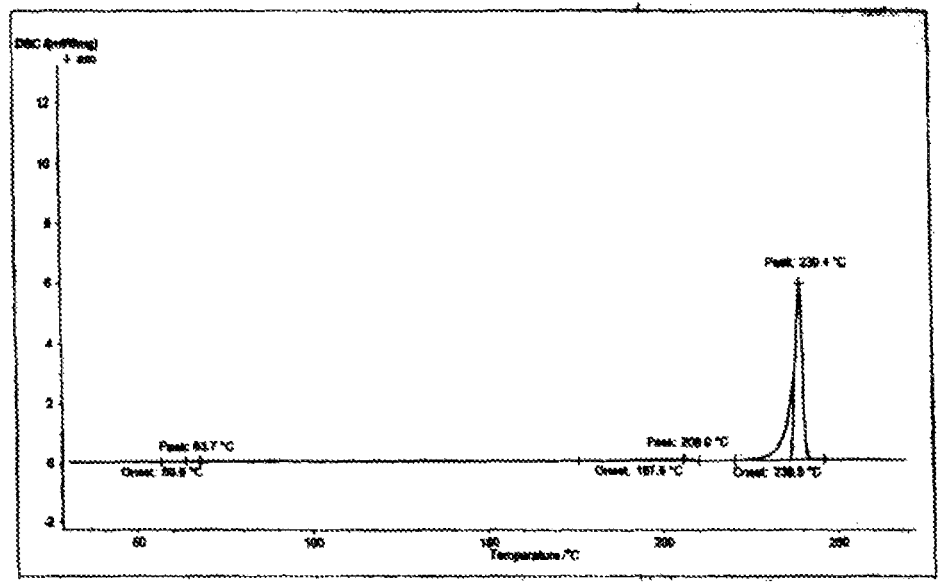
FIG. 5 is the differential scanning calorimetry (DSC) pattern of the chidamide crystal form A provided by Example 1 of the present invention. The ordinate represents heat flow rate expressed in cal/sec, and the abscissa represents temperature expressed in ° C.

Preparation of Chidamide Crystal Form A 4.84 kg chidamide (about 95% purity) was added to 20.91 kg 2 mol/L dilute hydrochloric acid solution, and dissolved by stirring at room temperature. Subsequently, 137.8 kg water was added and stirred for 5 min. To the resulted solution, 21.35 kg 2 mol/L NaOH solution was added dropwise, stirred for 30 min, and filtered. The resultant solid was added to 96.70 kg water, and subsequently, 8.39 kg 2 mol/L NaOH solution was added dropwise. The mixture was stirred for 60 min, filtered, and washed to a pH value of 5-7 with water. The resultant solid was dried under vacuum at 80° C. for 24 h to obtain 4.32 kg chidamide crystal form A with a purity of 99.2%. The X-ray powder diffraction pattern, infrared spectrum, and differential scanning calorimetry pattern of the crystal form were shown in FIG. 3, FIG. 4 and FIG. 5, respectively.

Example 2

Figure 6:
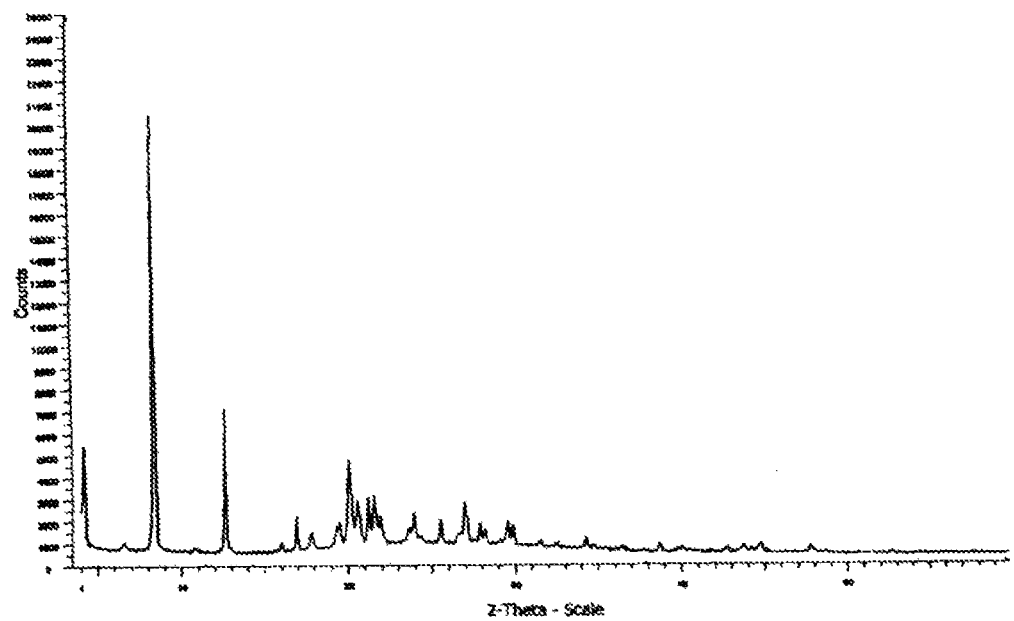
FIG. 6 is the X-ray powder diffraction pattern of the chidamide crystal form B provided in Example 3 of the present invention, which is obtained by irradiation with cooper Kα ray. In the X-ray powder diffraction pattern, the ordinate represents diffraction intensity expressed in counts per second (cps), and the abscissa represents diffraction angle 2θ expressed in degree.
Figure 7:
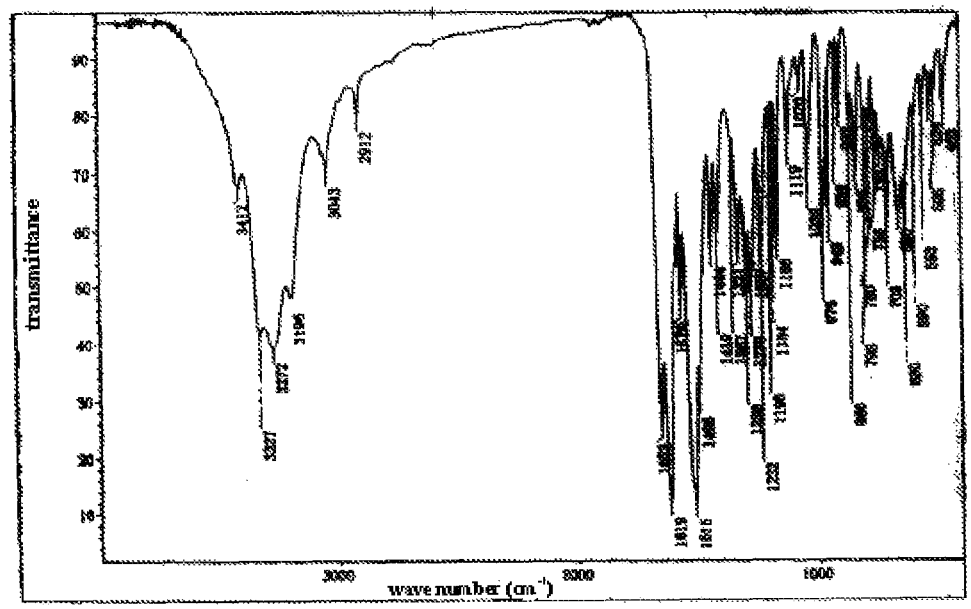
FIG. 7 is the infrared spectrum of the chidamide crystal form B provided by Example 3 of the present invention. The ordinate represents light transmittance (T) expressed in percentage (%); and the abscissa represents wave number expressed in $cm^{-1}$.
Figure 8:
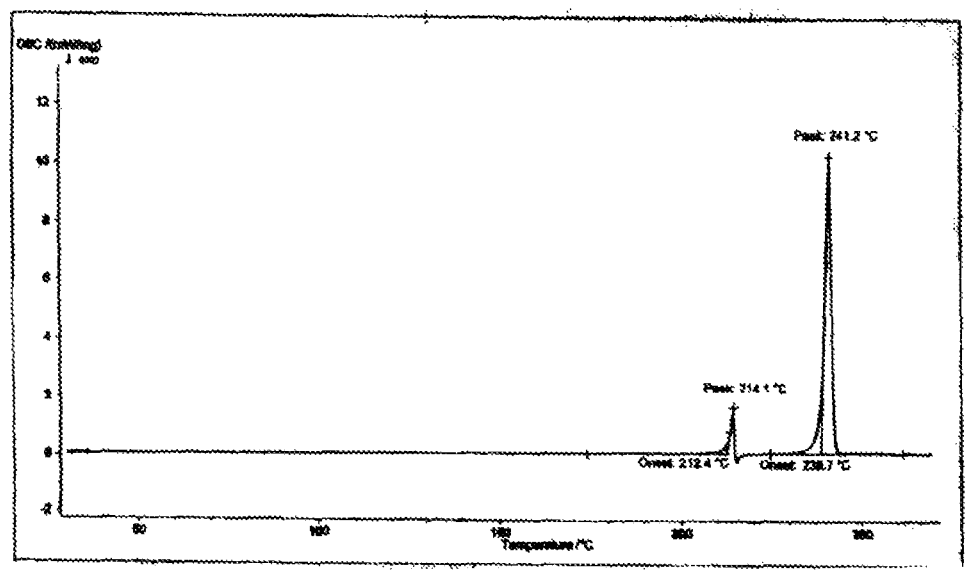
FIG. 8 is the differential scanning calorimetry (DSC) pattern of the chidamide crystal form B provided by Example 3 of the present invention. The ordinate represents heat flow rate expressed in cal/sec, and the abscissa represents temperature expressed in ° C.

Preparation of Chidamide Crystal Form B 1 g chidamide crystal form A was added to 10 mL dimethyl sulfoxide, and dissolved by stirring at room temperature. To the resultant solution, 100 mL water was added dropwise, stirred for 30 min, and filtered. The resultant solid was dried under vacuum at 80° C. for 24 h to obtain the chidamide crystal form B with a purity of 99.2%. The X-ray powder diffraction pattern, infrared spectrum, and differential scanning calorimetry pattern of the crystal form were shown in FIG. 6, FIG. 7 and FIG. 8, respectively.

Example 3

Preparation of Tablets of the Chidamide Crystal Form A

Formula (1000 tablets):

| | |
|---|---|
| Chidamide crystal form A | 5 g |
| Soluble starch | 50 g |
| Lactose | 20 g |
| Microcrystalline cellulose | 20 g |
| Sodium carboxymethyl starch | 8 g |
| Talc powder | 0.5 g |

The preparation process: chidamide crystal form A, lactose, soluble starch, microcrystalline cellulose and sodium carboxymethyl starch were each weighed out at the prescribed amount, and mixed uniformly. The mixture was wetted by a suitable amount of water to prepare the soft dough. Wet particulates were prepared using a 20-mesh sieve, and dried at 60° C. Particulates were sieved by using an 18-mesh sieve. Subsequently, talc powder was added at the prescribed amount and mixed uniformly. The tablets were obtained after being tabletted.

Example 4

Preparation of Capsules of the Chidamide Crystal Form A

Formula (1000 capsules):

| | |
|---|---|
| Chidamide crystal form A | 5 g |
| Microcrystalline cellulose | 55 g |
| Lactose | 35 g |
| Sodium carboxymethyl starch | 5 g |
| Magnesium stearate | 0.5 g |

The preparation process: the chidamide crystal form A was screened by passing through a 100-mesh sieve, and the microcrystalline cellulose, lactose, sodium carboxymethyl starch and magnesium stearate were screened by passing through a 80-mesh screen. The microcrystalline cellulose, lactose and sodium carboxymethyl starch were weighed out at the prescribed amounts, and mixed uniformly. Subsequently, the mixture was mixed with the chidamide crystal form A uniformly using equal increase method. After mixed with prescribed amount of magnesium stearate, the capsules were filled.

Example 5

Preparation of Granules of the Chidamide Crystal Form A

Formula (1000 bags):

| | |
|---|---|
| Chidamide crystal form A | 5 g |
| Soluble starch | 500 g |
| Lactose | 200 g |
| Microcrystalline cellulose | 175 g |
| Sodium carboxymethyl starch | 100 g |

The preparation process: chidamide crystal form A, lactose, soluble starch, microcrystalline cellulose and sodium carboxymethyl starch were each weighed out at the prescribed amounts, and mixed uniformly. The mixture was wetted by a suitable amount of water to prepare soft dough. Wet particulates were prepared using a 20-mesh screen, and dried at 60° C. Particulates were sieved by using an 18-mesh screen. After being filled, the granules were obtained.

Example 6

Preparation of Tablets of the Chidamide Crystal Form B

Formula (1000 tablets):

| | |
|---|---|
| Chidamide crystal form B | 5 g |
| Soluble starch | 50 g |
| Lactose | 20 g |
| Microcrystalline cellulose | 20 g |
| Sodium carboxymethyl starch | 8 g |
| Talc powder | 0.5 g |

The preparation process: chidamide crystal form B, lactose, soluble starch, microcrystalline cellulose and sodium carboxymethyl starch were each weighed out at the prescribed amount, and mixed uniformly. The mixture was wetted by a suitable amount of water to prepare soft dough. Wet particulates were sieved by using a 20-mesh screen, and dried at 60° C. Particulates were sieved by using an 18-mesh screen. Subsequently, talc powder was added at the prescribed amount and mixed uniformly. The tablets were obtained after being tabletted.

Example 7

Preparation of Capsules of the Chidamide Crystal Form B

Formula (1000 capsules):

| | |
|---|---|
| Chidamide crystal form B | 5 g |
| Microcrystalline cellulose | 55 g |
| Lactose | 35 g |
| Sodium carboxymethyl starch | 5 g |
| Magnesium stearate | 0.5 g |

The preparation process: the chidamide crystal form B was screened by passing through a 100-mesh sieve, and microcrystalline cellulose, lactose, sodium carboxymethyl starch and magnesium stearate were screened by passing through an 80-mesh screen. Microcrystalline cellulose, lactose and sodium carboxymethyl starch were weighed out at the prescribed amounts, and mixed uniformly. Subsequently, the mixture was mixed with the chidamide crystal form A uniformly using equal increase method. After mixed with prescribed amount of magnesium stearate, the capsules were filled.

Example 8

Preparation of Granule of the Chidamide Crystal Form B

Formula (1000 bags):

| | |
|---|---|
| Chidamide crystal form B | 5 g |
| Soluble starch | 500 g |

| | |
|---|---|
| Lactose | 200 g |
| Microcrystalline cellulose | 175 g |
| Sodium carboxymethyl starch | 100 g |

The preparation process: chidamide crystal form B, lactose, soluble starch, microcrystalline cellulose and sodium carboxymethyl starch were each weighed out at the prescribed amounts, and mixed uniformly. The mixture was wetted by a suitable amount of water to prepare soft dough. Wet particulates were sieved by using a 20-mesh screen, and dried at 60° C. Particulates were sieved by using an 18-mesh screen. After being filled, the granules were obtained.

The above examples are only described for understanding the methods and principal concepts of the present invention. It should be noted that some improvements and modifications can be made to the present invention by those skilled in the art without departing from the principles of the present invention. These improvements and modifications also fall within the scope of the claims of the present invention.

The invention claimed is:

1. Chidamide crystal form A, which is characterized in that its X-ray powder diffraction pattern has characteristic peaks at 2θ of about 4.18°, 6.61°, 8.42°, 12.69°, 17.85°, 18.34°, 19.27°, 20.10°, 20.59°, 21.58°, 23.70°, 23.96°, 25.52°, 27.00°, 27.90°, 29.59°, and 29.94°; its infrared spectrum has characteristic absorption peaks at about 3412, 3282, 3199, 3043, 1654, 1615, 1524, 1514, 1497, 1442, 1418, 1332, 1296, 1234, 1198, 1183, 1166 and 1027 cm$^{-1}$; and its differential scanning calorimetry pattern has a endothermic peak at about 239.4° C.

2. A method for preparing chidamide crystal form A having an X-ray powder diffraction pattern of the chidamide crystal form A with characteristic peaks at 2θ of about 4.18°, 6.61°, 8.42°, 12.69°, 17.85°, 18.34°, 19.27°, 20.10°, 20.59°, 21.58°, 23.70°, 23.96°, 25.52°, 27.00°, 27.90°, 29.59°, and 29.94°; an infrared spectrum with characteristic absorption peaks at about 3412, 3282, 3199, 3043, 1654, 1615, 1524, 1514, 1497, 1442, 1418, 1332, 1296, 1234, 1198, 1183, 1166 and 1027 cm$^{1}$; and a differential scanning calorimetry pattern with an endothermic peak at about 239.4° C., the method comprising:

Step 1: chidamide is added to 2 mol/L dilute hydrochloric acid solution, dissolved by stirring at room temperature and diluted with water; to the resultant solution is added dropwise 2 mol/L NaOH solution, stirred for 30 min, and then filtered; wherein the weight ratio between chidamide and the dilute hydrochloric acid solution in Step 1 is in the range from 1:4.2 to 1:4.4, the weight ratio between chidamide and water is in the range from 1:25 to 1:30, and the weight ratio between chidamide and NaOH solution is in the range from 1:2.5 to 1:2.7;

Step 2: the resultant solid is collected, and added to water; to the mixture is added dropwise 2 mol/L NaOH solution, stirred for 60 min, and then filtered; the resultant solid is collected, washed with water to a pH value from 5 to 7, and then dried; wherein the weight ratio between chidamide and water in Step 2 is in the range from 1:15 to 1:25, and the weight ratio between chidamide and NaOH solution is in the range from 1:1.5 to 1:2.0.

3. A pharmaceutical formulation for the treatment of cell differentiation and proliferation-related diseases, which is characterized in that the pharmaceutical formulation comprises the chidamide crystal form A according to claim 1, and pharmaceutically acceptable excipients.

* * * * *